US00PP11684P

United States Patent [19]

Glicenstein

[11] Patent Number: Plant 11,684

[45] Date of Patent: Dec. 12, 2000

[54] CHRYSANTHEMUM PLANT NAMED 'YOLUCY'

[75] Inventor: Leon Glicenstein, State College, Pa.

[73] Assignee: Yoder Brothers, Inc., Barberton, Ohio

[21] Appl. No.: 09/224,723

[22] Filed: Jan. 4, 1999

[51] Int. Cl.[7] ..... A01H 5/00

[52] U.S. Cl. ..... Plt./287

[58] Field of Search ..... Plt./287, 292, 291

[56] References Cited

PUBLICATIONS

UPOV–ROM, Feb. 1999, Plant Variety Database, GTI Jouve Retrieval Software, citation for 'Lucy', 2 citations for 'Yolucy'.

*Primary Examiner*—Howard J. Locker
*Attorney, Agent, or Firm*—C. A. Whealy

[57] ABSTRACT

A distinct cultivar of Chrysanthemum plant named 'Yolucy', characterized by its uniformly mounded and relatively tall plant habit; relatively late flowering; decorative-type inflorescences that are about 4.3 cm in diameter; attractive lavender pink ray florets; numerous inflorescences per plant; and excellent garden performance.

1 Drawing Sheet

BACKGROUND OF THE INVENTION

The present invention relates to a new and distinct cultivar of Chrysanthemum plant, botanically known as *Dendranthema grandiflora* and referred to by the cultivar name Yolucy.

The new cultivar is a product of a planned breeding program conducted by the Inventor in Salinas, Calif. The objective of the breeding program is to create new garden-type Chrysanthemum cultivars having inflorescences with desirable inflorescence forms and floret colors and good garden performance.

The new cultivar originated from a cross made by the Inventor in November, 1993, of the *Dendranthema grandiflora* cultivar Debonair (U.S. Plant Pat. No. 5,324) as the female, or seed, parent with an unidentified proprietary seedling selection as the male, or pollen, parent.

The cultivar Yolucy was discovered and selected by the Inventor as a flowering plant within the progeny of the stated cross in a controlled environment in Salinas, Calif., in January, 1995. The selection of this plant was based on its desirable inflorescence form and ray floret color and excellent garden performance.

Asexual reproduction of the new cultivar by terminal cuttings taken in a controlled environment in Salinas, Calif., has shown that the unique features of this new Chrysanthemum are stable and reproduced true to type in successive generations.

SUMMARY OF THE INVENTION

The cultivar Yolucy has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yolucy'. These characteristics in combination distinguish 'Yolucy' as a new and distinct cultivar:

1. Uniformly mounded and relatively tall plant habit.
2. Relatively late flowering.

3. Decorative-type inflorescences that are about 4.3 cm in diameter.
4. Attractive lavender pink ray florets.
5. Numerous inflorescences per plant.
6. Excellent garden performance.

The new Chrysanthemum is similar to the parent cultivar Debonair. However in side-by-side comparisons under commercial practice, plants of the new Chrysanthemum were more uniform in plant habit and flowered significantly later than plants of the cultivar Debonair.

BRIEF DESCRIPTION OF THE PHOTOGRAPHS

The accompanying photographs illustrate the overall appearance of the new cultivar.

The photograph at the top of the sheet comprises a side perspective view of a typical flowering plant of 'Yolucy'.

The phoptograph at the bottom of the sheet comprises a close-up view of typical inflorescences of the cultivar 'Yolucy'.

These photographs show the colors as true as it is reasonably possible to obtain in colored reproductions of this type. Floret and foliage colors in the photographs may differ from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Leamington, Ontario, Canada, under conditions which approximate those generally used in commercial garden Chrysanthemum production. One rooted cutting was planted in a 15-cm container on Jul. 20, 1998 and plants were grown outdoors under natural season conditions. Measurements and numerical values represent averages for typical flowering containers.

Botanical classification: *Dendranthema grandiflora* cultivar Yolucy.

Commercial classification: Decorative-type garden chrysanthemum.

Parentage:

*Female or seed parent.*—*Dendranthema grandiflora* cultivar Debonair, disclosed in U.S. Plant Pat. No. 5,324.

*Male or pollen parent.*—Unidentified proprietary seedling selection.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Perennial herbaceous decorative-type garden Chrysanthemum. Inverted triangle. Stems initially upright, then outwardly spreading giving a uniformly mounded appearance to the plant. Freely branching with lateral branches potentially developing at every node.

*Plant height.*—About 38 cm.

*Plant spread.*—About 48 cm.

*Foliage description.*—Leaf arrangement: Alternate. Length: About 7.1 cm. Width: About 6.2 cm. Apex: Acuminate. Base: Truncate. Margin: Palmately lobed, sinuses convergent. Texture: Upper surface sparsely pubescent; lower surface moderately pubescent. Veins prominent on lower surface. Petiole length: About 2.2 cm. Petiole diameter: About 3 mm. Color: Young foliage upper surface: 147A. Young foliage lower surface: 147B. Mature foliage upper surface: 147A. Mature foliage lower surface: 147B. Venation upper surface: 147A to 147B. Venation lower surface: 147B.

Inflorescence description:

*Appearance.*—Decorative-type inflorescence form with spatulate-shaped ray florets. Inflorescences borne on terminals above foliage, arising from leaf axils. Disk and ray florets arranged acropetally on a capitulum. One inflorescence per terminal with numerous inflorescences per plant.

*Flowering response.*—Under natural season conditions, plants flower in the autumn about 96 days after planting, and flower for at least three weeks.

*Inflorescence bud.*—Height: About 6 mm. Diameter: About 7.5 mm. Color: Close to 141A.

*Inflorescence size.*—Diameter: About 4.3 cm. Depth (height): About 1.6 cm. Diameter of disc: About 1 mm.

*Ray florets.*—Shape: Spatulate; long corolla tube. Length: About 2.1 cm. Width: About 6.5 mm. Apex: Emarginate. Margin: Entire. Texture: Smooth, glabrous, satiny. Orientation: Initially upright, then horizontal. Number of ray florets per inflorescence: Typically more than 250. Color: When opening, upper and lower surfaces: Close to 60D. Opened inflorescence: Upper surface: 68A to 73A; fading to 75C to 69A. Lower surface: 69A to 69B.

*Disc florets.*—Shape: Tubular, apex dentate. Length: About 3 mm. Width: Apex: About 1 mm. Base: About 1 mm. Number of disc florets per inflorescence: Typically fewer than five. Color: Immature: 154A. Mature: Apex: 13A. Mid-section and base: White.

*Peduncle.*—Aspect: Flexible, angled about 45° to the stem. Length: First peduncle: About 6.3 cm. Fourth peduncle: About 7.8 cm. Diameter: About 2.5 mm. Texture: Pubescent. Color: 141A.

*Reproductive organs.*—Androecium: Present on disc florets only. Anther color: Close to 9A, Pollen: Scarce. Gynoecium: Present on both ray and disc florets.

Disease resistance: Resistance to known Chrysanthemum diseases has not been observed on plants grown under commercial production conditions.

Seed production: Seed production has not been observed.

It is claimed:

1. A new and distinct cultivar of Chrysanthemum plant named 'Yolucy', as illustrated and described.

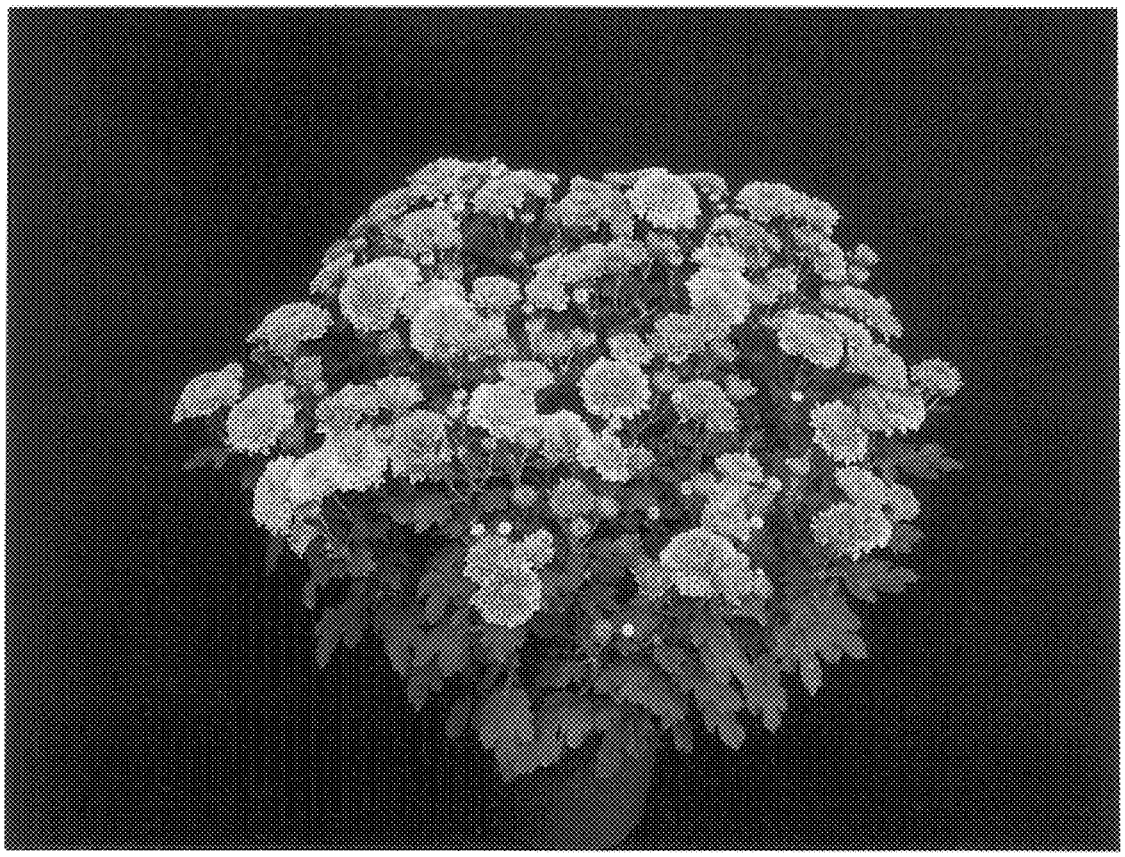
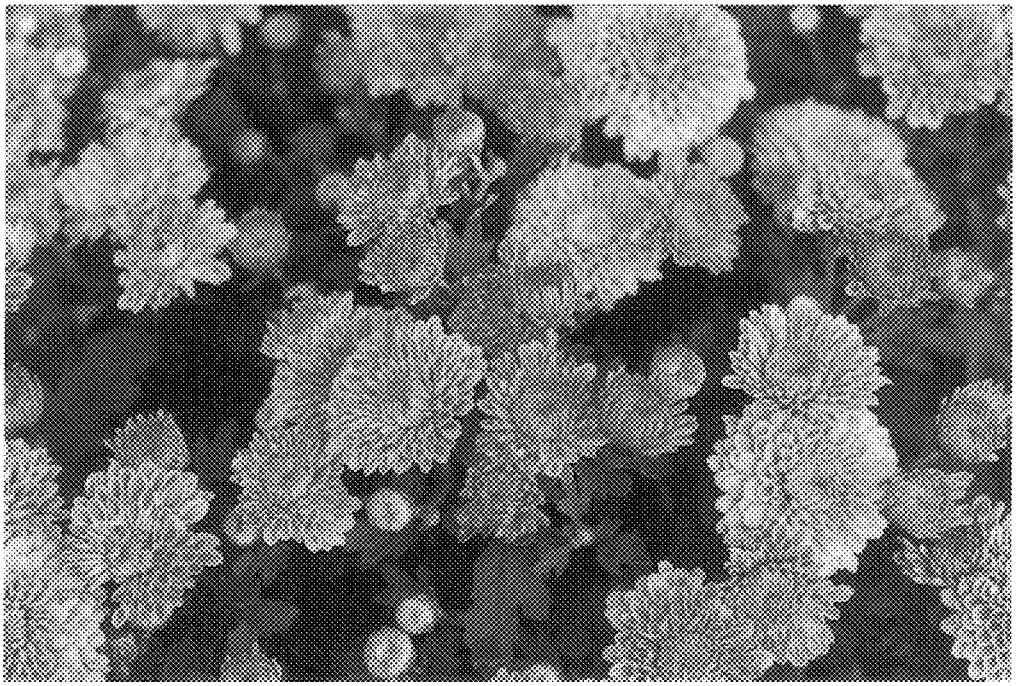

* * * * *